United States Patent [19]

Nishizawa et al.

[11] Patent Number: 4,795,544
[45] Date of Patent: Jan. 3, 1989

[54] ELECTROCHEMICAL GAS SENSOR

[75] Inventors: Hitoshi Nishizawa, Iwakura; Kazuyoshi Shibata, Nagoya, both of Japan

[73] Assignee: NGK Insulators, Ltd., Nagoya, Japan

[21] Appl. No.: 100,229

[22] Filed: Sep. 23, 1987

[30] Foreign Application Priority Data

Sep. 27, 1986 [JP] Japan .................. 61-228979

[51] Int. Cl.$^4$ .......................................... G01N 27/58
[52] U.S. Cl. ..................................... 204/425; 204/412
[58] Field of Search ............... 204/425, 410, 412, 15, 204/426

[56] References Cited

U.S. PATENT DOCUMENTS 4,645,572  2/1987  Nishizawa et al. ............ 204/1 T
4,650,560  3/1987  Ueno ............................ 204/410

OTHER PUBLICATIONS

Herman Dietz, Solid State Ionics 6, pp. 175–183, (1982).

Primary Examiner—G. L. Kaplan
Attorney, Agent, or Firm—Parkhurst, Oliff & Berridge

[57] ABSTRACT

A gas sensor for dealing with a measurement gas in an external space, having (a) an electrochemical pumping cell including a porous solid electrolyte body, and a first and a second electrode which are disposed on opposite sides of the porous solid electrolyte body, (b) a gas-tight ceramic body cooperating with a porous solid electrolyte body of the electrochemical pumping cell, to define therebetween an internal space, such that the first electrode substantially communicates with the internal space, and (c) a gas-tight solid electrolyte layer formed on or within the porous solid electrolyte body such that the first electrode is substantially entirely overlapped by the gas-tight solid electrolyte layer, as viewed in a direction perpendicular to a plane of the first electrode. The gas-tight solid electrolyte layer is formed to permit a portion of the porous solid electrolyte body to communicate with the internal space in the above-indicated direction.

10 Claims, 5 Drawing Sheets

ELECTROCHEMICAL GAS SENSOR

BACKGROUND OF THE INVENTION

1. Field of the Invention

The present invention relates generally to a gas sensor which uses a solid electrolyte for determining the concentration of a component in a gaseous fluid, and more particularly to such a gas sensor which is capable of stably providing a sharp characteristic curve and thereby effecting the measurement with significantly improved accuracy.

2. Disclosure of the Prior Art

There has been known a device which incorporates an electrochemical cell using a solid electrolyte. For example, such an electrochemical device is used as an oxygen sensor having an electrochemical cell which consists of an oxygen-ion conductive solid electrolyte such as zirconia ceramics, and a pair of porous electrodes, for determining the concentration of oxygen in an exhaust gas produced by an internal combustion engine of an automotive vehicle. In this type of sensor, an electrochemical pumping action is performed based on the reaction of the electrodes which occurs while an electric current is applied between the pair of electrodes. In the meantime, one of the porous electrodes is held in communication with a measurement gas in an external measurement-gas space, via suitable diffusion-resistance means such as a pin hole, a thin flat space or a porous ceramic layer, which provides a predetermined resistance to a diffusion of the measurement gas. The sensor provides an output in the form of a pumping current which corresponds to the oxygen concentration of the external measurement gas. Also known are electrochemical devices or gas sensors or detectors adapted to detect hydrogen, carbon dioxide, fuel gases, etc., by utilizing the principle based on the electrochemical pumping action and the diffusion resistance, as practiced in the oxygen sensor discussed above.

In one type of gas sensor using such an electrochemical cell (pumping cell) capable of performing an electrochemical pumping operation, the solid electrolyte body constituting the electrochemical cell is made porous so that it may function as a porous ceramic layer or diffusion-resistance means having a predetermined diffusion resistance. In this case, the porous solid electrolyte body is formed as a comparatively bulky mass on which a pair of electrodes are integrally formed. Accordingly, the measurement gas which diffuses through the interior of the bulky solid electrolyte mass to one of the electrodes takes different diffusion paths, whereby there arises a gradient in the concentration of the diffused measurement gas on the electrode. This gradient indicates an undesirable polarization characteristic, that is, insufficient sharpness of a characteristic curve (pumping current-pumping voltage curve) obtained by a pumping operation of the pumping cell, which results in a problem of inaccurate measurement of the measurement gas by the gas sensor.

Further, since the measurement gas diffuses also through the porous first and second electrodes of the electrochemical cell, the overall diffusion resistance of the cell is influenced by the gas permeability of the electrodes which may vary from time to time. This is another problem experienced in the known gas sensor discussed above.

SUMMARY OF THE INVENTION

The present invention was made in the light of the foregoing situations of the prior art. It is therefore an object of the invention to provide a gas sensor which is easy to manufacture and which includes a gas-tight solid electrolyte layer for restricting or defining a path of diffusion of a measurement gas through diffusion-resistance means in the form of a porous solid electrolyte body of an electrochemical pumping cell, so that the gas sensor is stably operable to provide a sharp polarization characteristic curve that permits accurate determination of concentration of a desired component in the measurement gas.

The above object may be achieved according to the principle of the present invention, which provides a gas sensor for dealing with a measurement gas in an external space, comprising (a) an electrochemical pumping cell including a porous solid electrolyte body, and a first and a second electrode which are disposed on opposite sides of the porous solid electrolyte body, (b) a gas-tight ceramic body cooperating with the porous solid electrolyte body of the electrochemical pumping cell, to define therebetween an internal space, such that the first electrode substantially communicates with the internal space, and (c) a gas-tight solid electrolyte layer formed on or within the porous solid electrolyte body such that the first electrode is substantially entirely overlapped by the gas-tight solid electrolyte layer, as viewed in a direction perpendicular to a plane of the first electrode. The gas-tight solid electrolyte layer permits a portion of the porous solid electrolyte body to communicate with the internal space in the above-indicated direction.

In the gas sensor of the present invention constructed as described above, the gas-tight solid electrolyte layer functions to restrict or limit a path of diffusion of the measurement gas through the porous solid electrolyte body between the exernal space and the internal space, so that the path of diffusion leads to the internal space, whereby the components of the measurement gas are mixed with each other within the internal space before the measurement gas contacts the first electrode. Therefore, the atmosphere adjacent to the first electrode can be effectively homogenized. In other words, the first electrode is less likely to be subject to an abnormal distribution of concentration of a certain component in the surrounding atmosphere. Accordingly, the instant gas sensor is stably operable to provide a sharp polarization characteristic curve necessary to assure accurate determination of the concentration of a desired component in the measurement gas.

According to the instant arrangement, at least the first electrode, or preferably the first and second electrodes is or are overlapped by the gas-tight solid electrolyte layer as viewed in the direction perpendicular to the first electrode. Consequently, the instant arrangement substantially prevents the measurement gas from diffusing through the first electrode or first and second electrodes. That is, the overall diffusion resistance of the gas sensor is not influenced by a timewise variation in the permeability of the electrode or electrodes, which affects the measuring accuracy of the sensor.

According to a preferred feature of the invention, the gas-tight solid electrolyte layer is at least partially embedded in the porous solid electrolyte body of the electrochemical pumping cell. Alternatively, the solid electrolyte layer is formed between the first or second electrode and one of the opposite major surfaces of the porous solid electrolyte body. In this case, the first or second electrode is disposed on the gas-tight solid electrolyte layer. Further, it is possible that the gas-tight solid electrolyte layer may be formed between the first electrode and one of the major surfaces of the porous solid electrolyte body, while another gas-tight solid electrolyte layer is disposed between the other surface of the porous solid electrolyte body and the second electrode. However, this second gas-tight solid electrolyte layer may be embedded within the porous solid electrolyte body.

The internal space to which the first electrode of the electrochemical pumping cell of the instant gas sensor is substantially exposed may be a thin flat space which has a predetermined diffusion resistance. In this case, bulk diffusion of the measurement gas within the thin flat space, in combination with the diffusion through the porous structure of the porous solid electrolyte body, makes it possible to adjust the dependence of a limit current to be obtained in the electrochemical pumping cell, upon the temperature and pressure of the measurement gas, over a relatively wide range.

According to a further feature of the invention, the first electrode has an annular shape, and the gas-tight solid electrolyte layer has a central aperture which is located radially inwardly of an inner periphery of the annular first electrode.

According to still a further feature of the invention, the first electrode, the gas-tight solid electrolyte layer, and the internal space are all rectangular in shape, as viewed in the direction perpendicular to the planes of these members. Further, the gas-tight solid electrolyte layer is formed on an inner surface of the porous solid electrolyte body so as to partially define the internal space, and to define an opening through which the porous solid electrolyte body communicates with the internal space, and the first electrode is formed on a portion of the gas-tight solid electrolyte layer which is exposed to the internal space.

According to a yet further feature of the invention, the gas-tight solid electrolyte layer has an aperture, and a portion of this solid electrolyte layer which defines the aperture is embedded in the porous solid electrolyte body such that the aperture communicates with the internal space through a portion of the porous solid electrolyte body, in the direction perpendicular to the porous solid electrolyte body. In this case, the first electrode is disposed on a portion of an inner surface of the porous solid electrolyte body which is exposed to the internal space.

In the gas sensor of the present invention, the concentration of a desired component in the measurement gas is determined according to the principle based on the diffusion resistance to the molecules of the component, and based on an electrochemical pumping of ions of the component through the porous solid electrolyte body between the first and second electrodes of the electrochemical pumping cell, upon application of an electric current between these two electrodes. However, it is possible to provide the gas sensor with another electrochemical cell (electrochemical sensing cell), which is operated according to the principle of a concentration cell, for detecting the atmosphere adjacent to the first electrode of the pumping cell which communicates with the internal space. This electrochemical cell provided in addition to the electrochemical pumping cell includes a second solid electrolyte body (gas-tight solid electrolyte), and a third and a fourth electrode which are formed on the second solid electrolyte body, such that the third electrode substantially communicates with the above-indicated internal space. This arrangement having the two electrochemical cells described above is advantageous for widening the range of applications of the sensor, and is one of the preferred embodiments of the invention.

In the case where the second electrochemical cell is provided, the second solid electrolyte body may constitute at least a portion of the gas-tight ceramic body which partially defines the internal space. Alternatively, the second solid electrolyte body may constitute a portion of the porous solid electrolyte body of the electrochemical pumping cell, or a portion of the gas-tight solid electrolyte layer. In either case, it is preferred that the third electrode be spaced apart from an inlet of the internal space, by a larger distance than the first electrode, in the direction parallel to the plane of the first or third electrode.

The gas tightness of the gas-tight solid electrolyte layer is determined such that an amount of diffusion of the measurement gas through the gas-tight solid electrolyte layer is almost negligible, as compared with an amount of diffusion of the same through the porous solid electrolyte body from the external space to the internal space. In other words, the gas-tight solid electrolyte layer is not required to be perfectly gas-tight.

BRIEF DESCRIPTION OF THE DRAWINGS

The above and optional objects, features and advantages of the present invention will become more apparent by reading the following detailed description of presently preferred embodiments of the invention, when considered in connection with the accompanying drawings, in which.

DETAILED DESCRIPTION OF THE PREFERRED EMBODIMENTS

To further clarify the present invention, the several presently preferred embodiments of the invention will be described in detail, by reference to the accompanying drawings.

Figure 1:
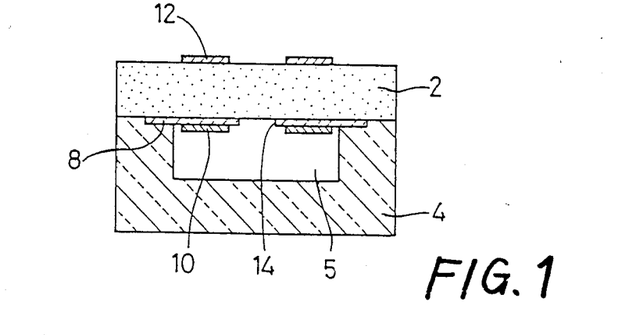
FIGS. 1 through 4 are elevational views in transverse cross section of different examples of simplest construction of a gas sensor according to the present invention.
Figure 2:
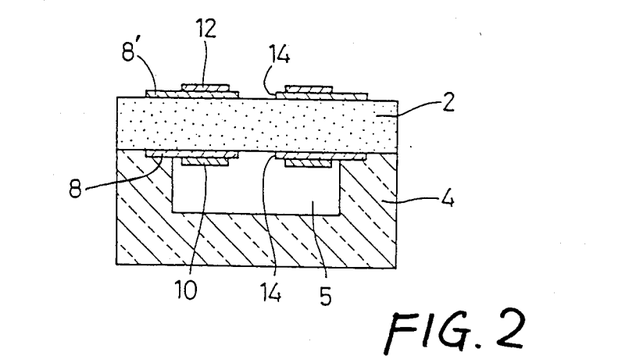

Referring first to the transverse cross sectional views of FIGS. 1 and 2, there are shown examples of basic construction of a gas sensor in the form of an oxygen sensor according to the principle of the present invention. In these examples, the oxygen sensor includes a one-piece mass consisting of a planar porous solid electrolyte body 2 having a predetermined resistance to a diffusion of a gas, and a generally planar gas-tight or dense zirconia ceramic body 4 superposed on the porous solid electrolyte body 2. The solid electrolyte body 2 and the ceramic body 4 cooperate with each other to define therebetween an enclosed, cylindrical internal space 5. The porous solid electrolyte body 2 may be a porous zirconia ceramic mass which is formed by firing a green or unfired mixture of a powdered zirconia ceramic material and a powdered sublimable material which sublimes at a firing temperature, as disclosed in U.S. Pat. No. 4,610,741 to Mase et. al.

In the oxygen sensor of FIG. 1, a gas-tight or dense solid electrolyte layer 8 is formed on one of opposite surfaces of the planar porous solid electrolyte body 2 which is exposed to the internal space 5. An annular first electrode 10 is formed on the gas-tight solid electrolyte layer 8, while an annular second electrode 12 is formed on the outer surface of the porous solid electrolyte body 2 such that the first and second electrodes 10, 12 are in concentric relation with each other. The two solid electrolyte members 2, 8, and the first and second electrodes 10, 12 constitute an integral electrochemical pumping cell. In the oxygen sensor of FIG. 2, the second electrode 12 is disposed on the porous solid electrolyte body 2 via another gas-tight solid electrolyte layer 8' (outer gas-tight solid electrolyte layer 8'), like the first electrode 10.

The inner and outer gas-tight solid electrolyte layers 8 and 8' disposed between the first electrode 10 or second electrode 12 and the porous solid electrolyte body 2 are made of a material similar to that of the solid electrolyte body 2. The solid electrolyte layers 8, 8' take the form of an annular shape which has a larger outside diameter than the first and second electrodes 10, 12, and a central aperture 14 which is concentric with the cylindrical internal space 5 and which is located radially inwardly of the inner periphery of the electrodes 10, 12. The electrodes 10, 12, gas-tight solid electrolyte layer 8 (FIG. 1) or layers 8, 8' (FIG. 2), and porous solid electrolyte body 2 form an integral one-piece construction. In this arrangement, the first electrode 10 is covered or overlapped the gas-tight solid electrolyte layer 8, as viewed in a direction perpendicular to the major surfaces of the first electrode 10, since the diameter of the central aperture 14 of the solid electrolyte layer 8 is smaller than the inside diameter of the first electrode 10. However, the aperture 14 permits a portion of the porous solid electrolyte body 2 to communicate with the internal space 5, in the direction specified above.

In the oxygen sensors constructed as described above, a measurement gas in an external measurement-gas space diffuses through the interior of the porous solid electrolyte body 2 under the predetermined diffusion resistance, and enters the internal space 5 through the central aperture 14 formed in the gas-tight solid electrolyte layer 8 (inner gas-tight solid electrolyte layer 8 in the arrangement of FIG. 2). The measurement gas introduced through the aperture 14 of the inner gas-tight solid electrolyte layer 8 then diffuses in the internal space 5 in the radial direction (right and left direction in FIGS. 1 and 2), whereby the introduced gas reaches the first electrode 10. In the present arrangement, the components of the introduced gas are effectively mixed evenly with each other in the internal space 5, whereby the concentration of the measurement gas contacting the first electrode 10 may be made even over the entire surface area of the electrode 10. Accordingly, the electrochemical pumping cell (2, 8, 8', 10, 12) is stably operable to provide a sharp polarization characteristic curve necessary to effect accurate determination of the measurement gas.

Stated differently, a path in which the measurement gas diffuses through the porous structure of the solid electrolyte body 2 is restricted or limited by the gas-tight solid electrolyte layer 8, such that the measurement gas is permitted to communicate with the internal space 5 only through the central aperture 14 of the inner gas-tight solid electrolyte layer 8. Therefore, the introduced measurement gas adjacent to the first electrode 10 is less likely to have an uneven distribution of concentration of the component to be measured, since the measurement gas diffuses through substantially the same portion of the porous solid electrolyte body 2, which substantially defines the restricted path of diffusion of the gas leading to the central aperture 14 communicating with the internal space 5. As a result, the electrochemical pumping cell may maintain a comparatively constant or uniform polarization characteristic, which is advantageous to improve the sensing accuracy of the sensor.

In the present sensor, a DC current from an external power source is applied between the first and second electrodes 10, 12 of the electrochemical pumping cell, as is well known in the art, so that ions of a desired component (oxygen ions in the illustrated embodiments) of the measurement gas are moved from the first electrode 10 to the second electrode 12, or vice versa, whereby the component from the external measurement-gas space diffuses through the porous solid electrolyte body 2 and the internal space 5, and reaches the first electrode 10. The concentration of the component whose ions are moved between the electrodes 10, 12, or the concentration of a component which chemically reacts with the diffused component, is detected in an ordinary manner, by means of an ammeter or a potentiometer.

Figure 3:
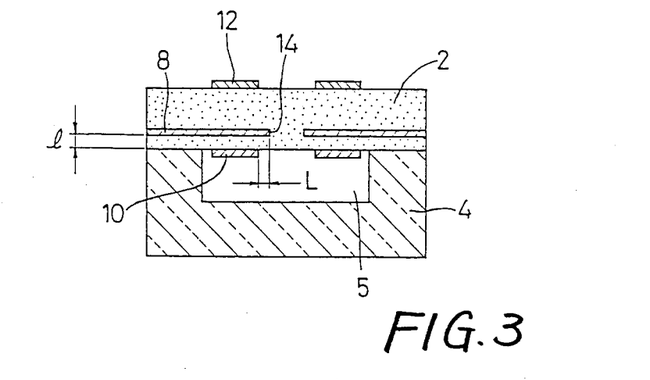
Figure 4:
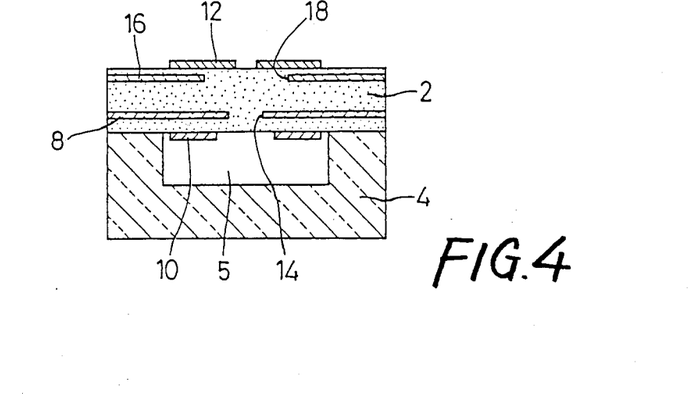

While the gas-tight solid electrolyte layer 8 of the oxygen sensors described above is formed on the inner surface of the porous solid electrolyte body 2, the solid electrolyte layer 8 may be embedded within the porous solid electrolyte body 2 such that the layer 8 is positioned relatively adjacent to the first electrode 10, as illustrated in FIGS. 3 and 4. In this embodiment, too, the central aperture 14 of the gas-tight solid electrolyte layer 8 is located radially inwardly of the inner periphery of the annular first electrode 10, that is, the entire area of the first electrode 10 is overlapped by the gas-tight solid electrolyte layer 8, as viewed in the vertical direction of FIGS. 3 and 4, i.e., in the direction perpendicular to the plane of the first electrode 10.

In these modified sensors, too, the diffusion path of the measurement gas through the porous solid electrolyte body 2 is restricted or limited by the gas-tight solid electrolyte layer 8, so that the measurement gas is introduced into the internal space 5 primarily through the central aperture 14 of the gas-tight solid electrolyte layer 8. Therefore, the concentration of the introduced measurement gas whose components are mixed within the space 5 and which contacts the first electrode 10 is effectively made even over the entire area of the first electrode 10, as in the preceding embodiments.

In the present modified embodiments, the first electrode 10 directly contacts the porous solid electrolyte body 2 as a result of the embedding of the gas-tight solid electrolyte layer 8 within the solid electrolyte body 2. This arrangement provides the following advantage. Namely, the instant arrangement is advantageous for preventing or alleviating a problem of deterioration of the solid electrolyte due to otherwise possible blackening which may occur during an electrochemical pumping operation to move ions from the first electrode 10 toward the second electrode 12. This advantage can be enjoyed because of a reduced possibility that the electrode (10) has a concentration gradient of the measurement gas within its interior structure in the direction of thickness, and a reduced possibility of an extremely low concentration at a certain local point within the electrode, in the case where one of the major opposite surfaces of the electrode communicates with the internal space (5) while the other major surface contacts the porous solid electrolyte body (2), as compared with the case where the electrode contacts the gas-tight solid electrolyte layer (8). Even if the porous solid electrolyte body (2) is more or less blackened, the solid electrolyte body may be easily restored since the porous body (2) has a comparatively large surface area.

In the present arrangement wherein the first electrode (10) contacts the solid electrolyte (2) which is porous, the first electrode has a higher degree of activity, than in the case where the electrode contacts a gas-tight solid electrolyte.

Unlike the preceding embodiments, the present modified embodiments having the gas-tight solid electrolyte layer 8 embedded in the porous solid electrolyte body 2 tends to have reduced evenness of concentration of the atmosphere adjacent to the first electrode 10, since the atmosphere surrounding the first electrode is influenced by a measurement gas stream (A) which diffuses through the porous solid electrolyte body 2 in the lateral direction (horizontal direction in FIGS. 3 and 4) and reaches the first electrode 10, without passing through the internal space 5, and a measurement gas stream (B) which passes through the central aperture 14 of the gas-tight solid electrolyte layer 8 and directly reaches the back surface of the first electrode 10 which contacts the porous solid electrolyte body 2. However, the influence of the stream (A) can be diminished by reducing a distance l between the first electrode 10 and the gas-tight solid electrolyte layer 8. If the sensor is constructed as described below such that the gas-tight solid electrolyte layer 8 directly contacts the gas-tight ceramic body 4, the influence of the gas stream (A) can be completely eliminated. Further, the influence of the gas steam (B) can be reduced to a negligible extent by providing a relatively large distance L between the inner peripheries of the first electrode 10 and the gas-tight solid electrolyte layer 8 (between the inside diameters of these annular members) in the direction parallel to the plane of the electrode 10, in relation to the above-indicated distance l.

As illustrated in FIG. 4, the oxygen sensor may have at least one second gas-tight solid electrolyte layer 16 with a central aperture 18, in addition to the first gas-tight solid electrolyte layer 8 which serves to restrict the path of diffusion of the measurement gas into the internal space 5. In this instance, it is not necessary that the entire area of the first electrode 10 is overlapped by the second gas-tight solid electrolyte layer 16, as viewed in the direction perpendicular to the plane of the first electrode. In other words, the diameter of the central aperture 18 of the second gas-tight solid electrolyte layer 16 may be larger than the inside diameter of the first electrode 10.

The gas sensor of the present invention is by no means limited to the above-illustrated constructions, but the principle of the invention may be effectively embodied as the gas sensor having other constructions as illustrated in FIGS. 5 through 10.

Figure 5:
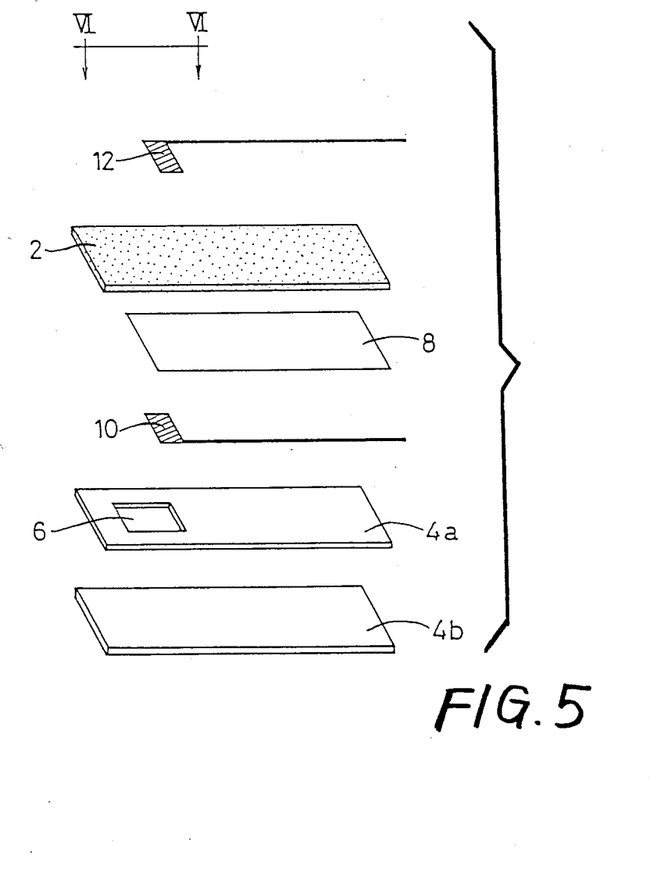
FIGS. 5, 7 and 9 are perspective explanatory views of different embodiments of the gas sensor of the invention.
Figure 6:
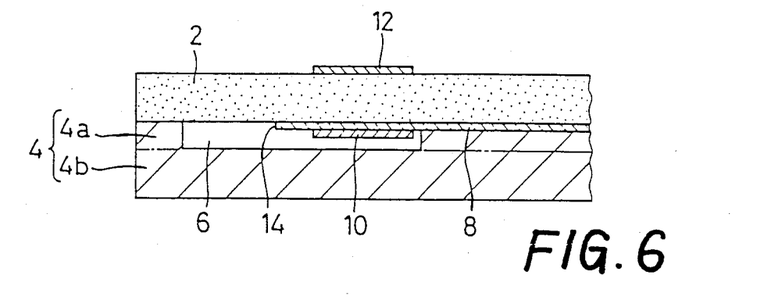
FIGS. 6, 8 and 10 are elevational views in cross section taken along line VI—VI of FIG. 5, line VIII—VIII of FIG. 7 and line X—X of FIG. 9, respectively.

The gas sensor shown in FIGS. 5 and 6 is a modification of the basic embodiment of FIG. 1. In this modified embodiment, the first and second electrodes 10, 12 have a rectangular shape, and the first electrode 10 is disposed on the inner surface of the porous solid electrolyte body 2 via the rectangular gas-tight solid electrolyte layer 8. The second electrode 12 is formed directly on the other or outer surface of the porous solid electrolyte body 2. Thus, an electrochemical pumping cell is provided.

The gas-tight ceramic body 4 is an integral body consisting of a first dense ceramic layer 4a having a cutout, and a second dense ceramic layer 4b on which the first ceramic layer 4a is superposed. The cutout formed in the first ceramic layer 4a gives an internal space in the form of a rectangular thin flat space 6 having a predetermined diffusion resistance. The first electrode 10 and the gas-tight solid electrolyte layer 8 are formed on the porous solid electrolyte body 2 such that the first electrode 10 communicates with the thin flat space 6, while the gas-tight solid electrolyte layer 8 partially closes the above-indicated cutout in the first ceramic layer 4aa, so as to partially define an opening 14 through which the porous solid electrolyte body 2 communicates with the thin flat space 6. In this embodiment, too, the entire area of the first electrode 10 is covered by or is overlapped by the gas-tight solid electrolyte layer 8, as viewed in the direction perpendicular to the plane of the first electrode.

In the present gas sensor, the gas-tight solid electrolyte layer 8 determines the width of the opening 14 of the thin flat space 6, and the measurement gas which has diffused through the porous solid electrolyte body 2 is introduced into the thin flat space 6 through the opening 14. The introduced measurement gas then moves through the thin flat space 6 in the horizontal direction (in FIG. 6), and reaches the first electrode 10.

Figure 7:
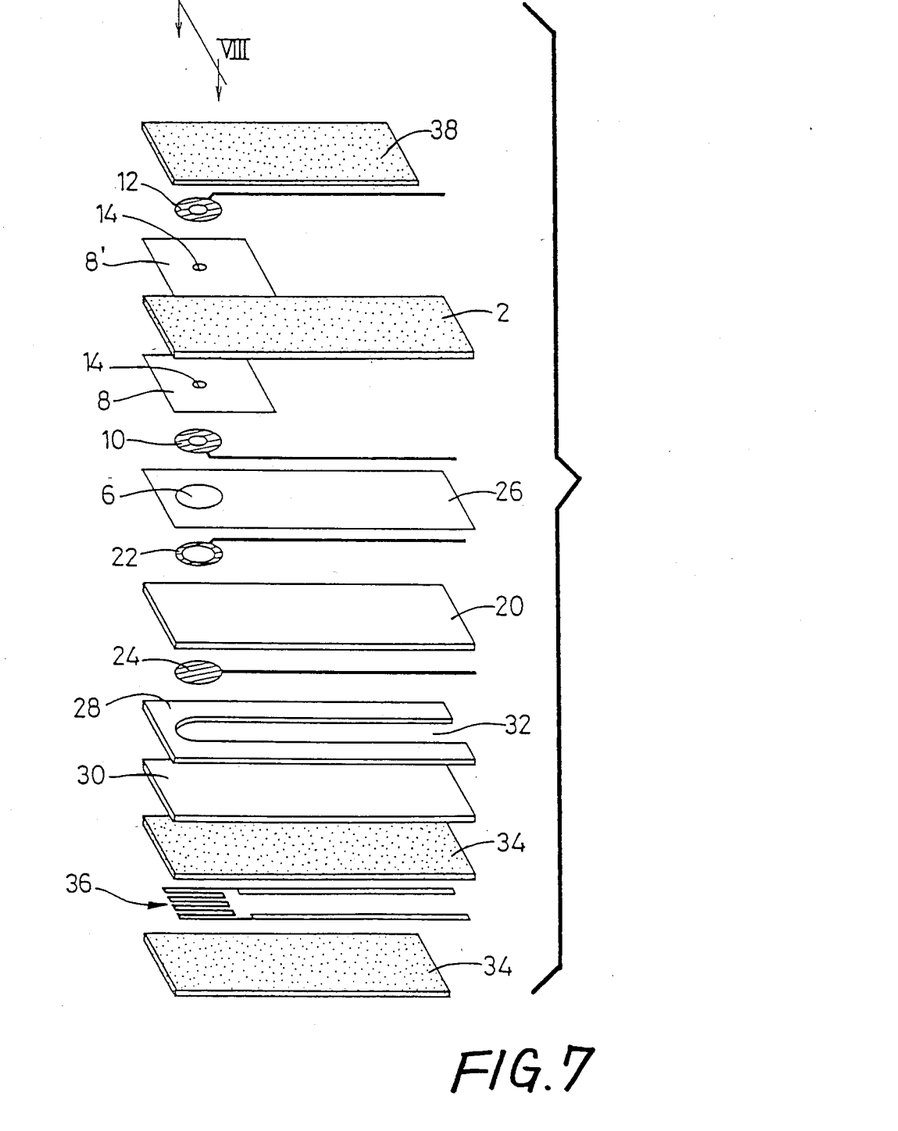
Figure 8:
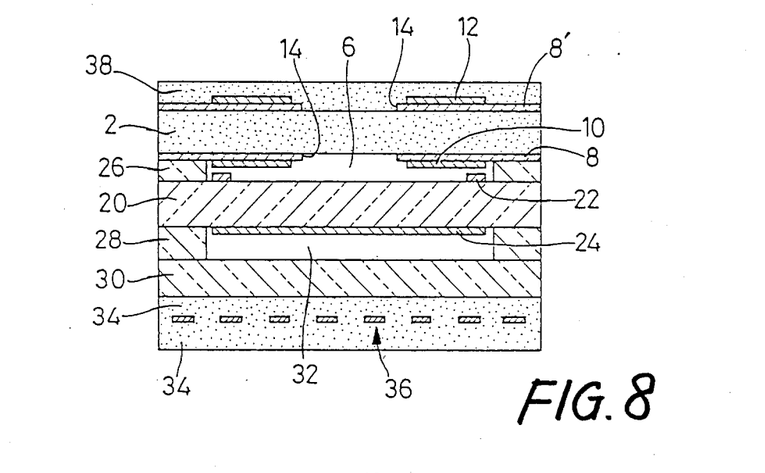

The gas sensor shown in FIGS. 7 and 8 is characterized in that the sensor has an electrochemical sensing cell in addition to an electrochemical pumping cell. The pumping cell is constituted by an integral laminar structure consisting of a planar porous solid electrolyte body 2, two gas-tight or dense solid electrolyte layers 8, 8' and first and second electrodes 10, 12 formed on the respective solid electrolyte layers 8, 8'. The sensing cell consists of a gas-tight solid electrolyte plate 20 which forms a part of a gas-tight ceramic of the sensor, and third and fourth electrodes 22, 24 which are integrally formed on the opposite surfaces of the solid electrolyte plate 20.

The third electrode 22 communicates with a thin flat space 6 which has a predetermined diffusion resistance. The thin flat space 6 is formed in a planar spacer layer 26 which is interposed between the sensing and pumping cells and which is made of a gas-tight ceramic material. The third electrode 22 functions as a measuring electrode exposed to an atmosphere adjacent to the first electrode 10, which also communicates with the thin flat space 6.

On one side of the electrochemical sensing cell on which the fourth electrode 24 is disposed, a planar spacer member 28 and a covering member 30 which are both formed of a gas-tight ceramic material are superposed on the gas-tight solid electrolyte plate 20. The spacer member 28 has a cutout which cooperates with the plate 20 and the covering member 30 to define an air passage 32. The fourth electrode 24 is positioned so as to communicate with this air passage 32, and to function as a reference electrode exposed to an ambient air as a reference gas, which is introduced into the air passage 32 through its open end.

On the outer surface of the covering member 30, there is formed heater means which consists of a heating element 36, and electrically insulating layers 34, 34 formed of alumina or similar ceramic material so as to embed the heating element 36. Thus, the instant gas sensor or its sensing cell has the built-in heater means.

Further, the electrochemical pumping cell has a porous ceramic protective layer 38 formed on the outer surface of the porous solid electrolyte body 2 on which the second electrode 12 is disposed. The protective layer 38 protects the second electrode 12 against direct exposure to the measurement gas in the external measurement-gas space, while permitting the same electrode 12 to communicate with the external measurement gas.

In the gas sensor constructed as described above, a DC current is applied between the first and second electrodes 10, 12 of the electrochemical pumping cell, so that the external measurement gas diffuses through the porous solid electrolyte body 2 into the thin flat space 6, while the diffusion path is restricted by the gas-tight solid electrolyte layer 8, and the atmosphere adjacent to the first electrode 10 is controlled by the pumping action of the pumping cell. In the meantime, the concentration of a desired component of the thus controlled atmosphere adjacent to the first electrode 10 is detected by the electrochemical sensing cell, in a manner known in the art. Briefly, an electromotive force is induced between the third and fourth electrodes 22, 24, due to a difference in the concentration of the component between the atmospheres to which these two electrodes 22, 24 are exposed. The induced electromotive force is applied to an external detecting device to determine the concentration of the component near the third electrode 22.

In the present embodiment, the heating element 36 is energized by an external power source, to maintain the solid electrolyte material (2, 8, 8', 20) and the electrodes (10, 12, 22, 24) of the electrochemical oxygen sensor (gas sensor) at optimum operating temperatures to assure a precise sensing operation, even when the temperature of the measurement gas is relatively low.

Figure 9:
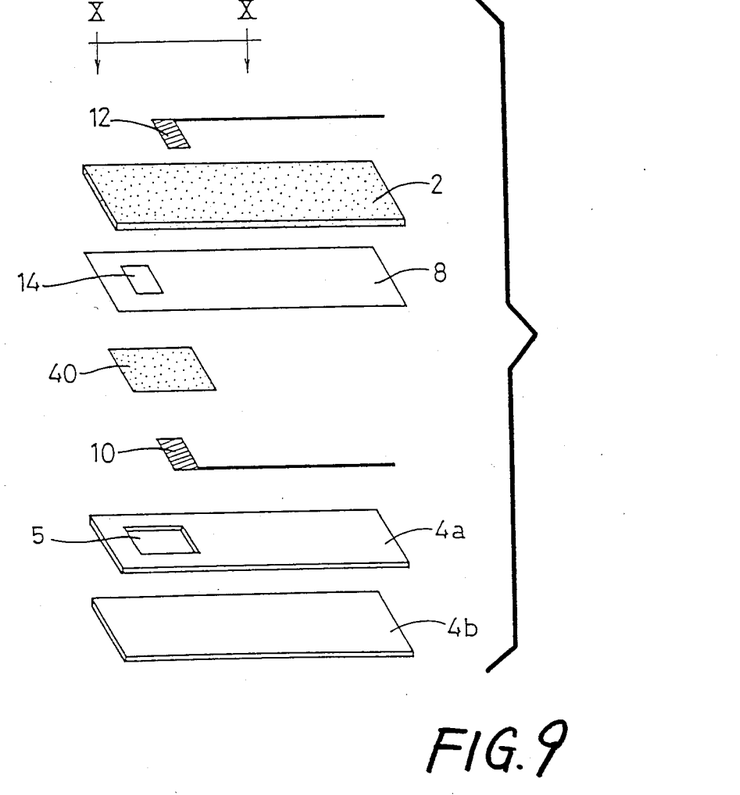
Figure 10:
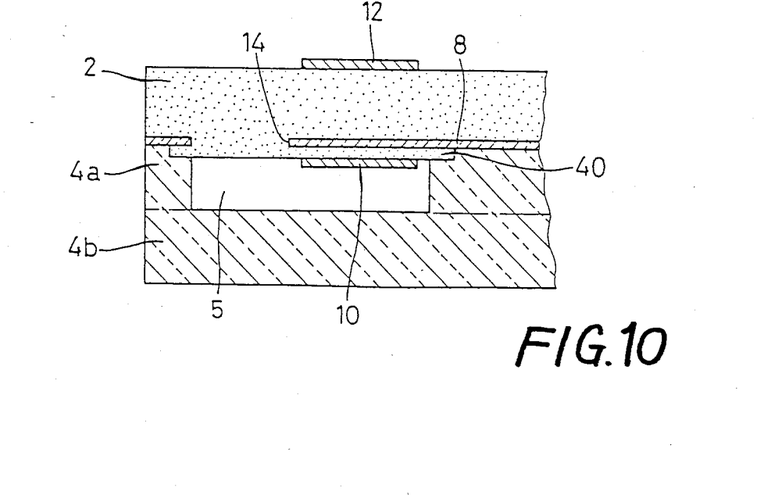

The gas sensor shown in FIGS. 9 and 10 is different from the gas sensor of FIGS. 5 and 6, in that the gas-tight solid electrolyte layer 8 of FIGS. 9 and 10 is embedded in the porous solid electrolyte body 2. Described more specifically, the porous solid electrolyte body 2 includes as an integral part thereof a porous solid electrolyte layer 40 made of the same solid electrolyte material. The gas-tight solid electrolyte layer 8 has a rectangular aperture 14, and the porous solid electrolyte layer 40 is formed so that a portion of the gas-tight solid electrolyte layer 8 surrounding or defining the aperture 14 is embedded in the porous solid electrolyte body 2 such that the aperture 14 communicates with the internal space 5 through a portion of the layer 40 in a direction perpendicular to the plane of the layer 8, as indicated in FIG. 10. The first electrode 10 is formed on a portion of the porous solid electrolyte layer 40 exposed to the internal space 5, so that the first electrode 10 communicates with the internal space 5, and such that the first electrode 10 is entirely overlapped by the embedded portion of the gas-tight solid electrolyte layer 8.

In the present embodiment wherein the gas-tight solid electrolyte layer 8 is partially embedded in the porous solid electrolyte body 2, the porous solid electrolyte layer 40 between the first electrode 10 and the gas-tight solid electrolyte layer 8 is protected from direct exposure to the external measurement gas. That is, the gas-tight solid electrolyte layer 8 directly contacts the gas-tight ceramic body 4 (more precisely, the dense ceramic layer 4a) at the end of the porous solid electrolyte layer 40 (left-hand side end as seen in FIG. 10). This arrangement substantially eliminates otherwise possible introduction of the measurement gas into the porous solid electrolyte layer 40 through its end face, and consequent diffusion of the measurement gas through the layer 40 to the first electrode 10.

In the gas sensors which have been illustrated, the porous or gas-tight solid electrolyte members of the electrochemical pumping and sensing cells, and the gas-tight solid electrolyte layers are made of known ion-conductive solid electrolyte materials, for example, oxygen-ion conductive solid electrolytes such as zirconia ceramics or a solid solution of $Bi_2O_3$-$Y_2O_3$, proton-conductive solid electrolytes such as $SrCe_{0.95}Yb_{0.05}O_{3-a}$, electrolytes such as $CaF_2$.

The electrodes 10, 12, 22, 24 of the electrochemical cells are made of metals such as platinum, rhodium palladium gold and nickel or conductive compounds such as tin oxide. Preferably, the electrodes have a porous structure. According to one preferred method of forming the electrodes, a material consisting principally of a metal or conductive compound indicated above is applied by printing to the respective solid electrolyte, and the applied material is fired into the suitably formed electrodes, and leads or conductor strips extending from the electrodes. To avoid flake-off or separation of the electrodes and their leads from the solid electrolyte bodies or members, or disconnection or breakage of the leads, it is desirable that the material of the electrodes and leads contains a powdered ceramic material such as zirconia, yttria or alumina, so that the fired electrodes and leads may be integrally bonded to the contacting surface of the solid electrolyte, with an increased adhesive force.

A green laminar structure of the gas sensors according to the invention may be prepared in a known lamination or screen-printing process, and the prepared green laminar structure may be co-fired in a suitable process also known in the art. The porous solid electrolyte body 2 of the electrochemical pumping cell is made of a solid electrolyte material whose sintering or firing temperature is different from that of the materials of the gas-tight ceramic body 4 and gas-tight solid electrolyte layer 8. It is possible that the material of the porous solid electrolyte body 2 may contain a substance which disappears upon firing thereof.

While the present invention has been described in its presently preferred embodiments or examples, it is to be understood that the invention is not limited to the precise details of construction of the illustrated embodiments, but may be embodied with various changes, modifications and improvements which may occur to those skilled in the art, without departing from the spirit and scope of the invention defined in the appended claims.

As is apparent from the foregoing description, the gas sensor constructed according to the present invention is capable of stably producing a sharp polarization characteristic curve which permits highly precise determination of concentration of a desired component in the measurement gas, owing to even distribution of concentration of the measurement gas which contacts the first electrode communicating with the internal space. This advantage is conducive to the gas-tight solid electrolyte layer which serves to restrict or define the path of diffusion of the measurement gas through the porous solid electrolyte body of the electrochemcal pumping cell, so that the measurement gas which has diffused through the solid electrolyte body is once introduced into the internal space before the measurement gas reaches the first electrode.

Although the gas sensor according to the invention is suitably used as a sensor for dealing with rich-burned or lean-burned exhaust gases emitted from an engine of an automotive vehicle, the instant gas sensor may also be used as an oxygen sensor for determining the oxygen concentration of exhaust gases produced as a result of combustion of an air-fuel mixture having a stoichiometric air/fuel ratio. Further, the instant gas sensor may be used as other sensors, detectors or controllers adapted to detect hydrogen, carbon dioxides and other components of a fluid which are associated with electrode reaction.

What is claimed is:

1. A gas sensor for dealing with a measurement gas in an external space comprising:
   an electrochemical pumping cell including a porous solid electrolyte body, and a first and a second electrode which are disposed on opposite sides of said porous solid electrolyte body;
   a gas-tight ceramic body cooperating with said porous solid electrolyte body of the electrochemical pumping cell, to define therebetween an internal space, such that said first electrode substantially communicates with said internal space;
   a gas-tight solid electrolyte layer formed on or within said porous solid electrolyte body such that said first electrode is substantially entirely overlapped by said gas-tight solid electrolyte layer, as viewed in a direction perpendicular to a plane of said first electrode, said gas-tight solid electrolyte layer permitting a portion of said porous solid electrolyte body to communicate with said internal space in said direction.

2. A gas sensor according to claim 1, wherein said second electrode is substantially entirely overlapped by said gas-tight solid electrolyte layer, as viewed in a direction perpendicular to a plane of said second electrode.

3. A gas sensor according to claim 1, wherein said gas-tight solid electrolyte layer is formed between said first electrode, and one of opposite major surfaces of said porous solid electrolyte body, said first electrode being disposed on said gas-tight solid electrolyte layer.

4. A gas sensor according to claim 1, wherein said gas-tight solid electrolyte layer is formed between said second electrode, and one of opposite major surfaces of said porous solid electrolyte body, said second electrode being disposed on said gas-tight solid electrolyte layer.

5. A gas sensor according to claim 1, wherein said gas-tight solid electrolyte layer is formed between said first electrode and one of opposite major surfaces of said porous solid electrolyte body, said gas sensor further comprising another gas-tight solid electrolyte layer formed between said second electrode and the other of said opposite major surfaces of said porous solid electrolyte body, said first and second electrodes being disposed on said gas-tight solid electrolyte layer and said another gas-tight solid electrolyte layer, respectively.

6. A gas sensor according to claim 1, wherein at least a portion of said gas-tight solid electrolyte layer is embedded within said porous solid electrolyte body, and said first electrode is disposed in contact with one of opposite major surfaces of said porous solid electrolyte body.

7. A gas sensor according to claim 1, further comprising another gas tight solid electrolyte layer formed on or within said porous solid electrolyte body.

8. A gas sensor according to claim 1, wherein said first electrode has an annular shape, and said gas-tight solid electrolyte layer has a central aperture which is located radially inwardly of an inner periphery of said annular first electrode.

9. A gas sensor according to claim 1, wherein said first electrode, said gas-tight solid electrolyte layer, and said internal space are rectangular in shape, said gas-tight solid electrolyte layer being formed on an inner surface of said porous solid electrolyte body so as to partially define said internal space, and to define an opening through which said porous solid electrolyte body communicates with said internal space, said first electrode being formed on a portion of said gas-tight solid electrolyte layer which is exposed to said internal space.

10. A gas sensor according to claim 1, wherein said gas-tight solid electrolyte layer has an aperture, and a portion of said gas-tight solid electrolyte layer defining said aperture is embedded in said porous solid electrolyte body such that said aperture communicates with said internal space through a portion of said porous solid electrolyte body in said direction, said first electrode being disposed on a portion of an inner surface of said porous solid electrolyte body which is exposed to said internal space.

* * * * *